(12) United States Patent
Fukuhara

(10) Patent No.: US 11,497,660 B2
(45) Date of Patent: Nov. 15, 2022

(54) METHOD FOR MANUFACTURING COMPOSITE SHEET

(71) Applicant: ZUIKO CORPORATION, Settu (JP)

(72) Inventor: Takeshi Fukuhara, Settu (JP)

(73) Assignee: ZUIKO CORPORATION, Osaka (JP)

( * ) Notice: Subject to any disclaimer, the term of this patent is extended or adjusted under 35 U.S.C. 154(b) by 360 days.

(21) Appl. No.: 16/841,159

(22) Filed: Apr. 6, 2020

(65) Prior Publication Data

US 2020/0237578 A1 Jul. 30, 2020

Related U.S. Application Data

(62) Division of application No. 15/575,145, filed as application No. PCT/JP2016/064428 on May 16, 2016.

(30) Foreign Application Priority Data

Jun. 8, 2015 (JP) .............................. JP2015-116142

(51) Int. Cl.
| | |
|---|---|
| *A61F 13/513* | (2006.01) |
| *A61F 13/15* | (2006.01) |
| *A61F 13/511* | (2006.01) |
| *B32B 3/28* | (2006.01) |
| *B32B 5/02* | (2006.01) |
| *B32B 37/10* | (2006.01) |
| *B31F 1/07* | (2006.01) |

(52) U.S. Cl.
CPC ............ *A61F 13/513* (2013.01); *A61F 13/15* (2013.01); *A61F 13/1565* (2013.01); *A61F 13/15707* (2013.01); *A61F 13/511* (2013.01); *A61F 13/51104* (2013.01); *B31F 1/07* (2013.01); *B32B 3/28* (2013.01); *B32B 5/022* (2013.01); *B32B 37/10* (2013.01); *A61F 2013/15715* (2013.01); *A61F 2013/51338* (2013.01); *B31F 2201/0764* (2013.01); *B31F 2201/0774* (2013.01)

(58) Field of Classification Search
CPC ...... B31F 2001/0774; B31F 2001/0764; B31F 1/07
See application file for complete search history.

(56) References Cited

U.S. PATENT DOCUMENTS

| | | | | |
|---|---|---|---|---|
| 3,708,366 | A * | 1/1973 | Donnelly | .................. B31F 1/07 156/219 |
| 8,557,075 | B2 * | 10/2013 | Gelli | ........................ B31F 1/07 156/209 |

(Continued)

*Primary Examiner* — Barbara J Musser
(74) *Attorney, Agent, or Firm* — Manabu Kanesaka

(57) ABSTRACT

A method for manufacturing a composite sheet includes a first step of, in a state that a curved part of a first sheet whose one surface rises and whose another surface is recessed and that a second sheet is overlaid on the first sheet, revolving a first roller to convey the first sheet and the second sheet; a second step of passing the sheets between the first roller and a second roller revolving so that a pressing part protruding outward in the radial direction from the outer peripheral surface of the second roller is inserted into the recess of the first roller; forming, in a region within the second sheet opposing the curved part, a protruding part which is surrounded by a flat part; and a third step of joining a boundary part of the first sheet to the second sheet.

4 Claims, 6 Drawing Sheets

(56) References Cited

U.S. PATENT DOCUMENTS

2002/0160155 A1* 10/2002 Muller .................. B32B 7/05
428/196
2010/0183850 A1* 7/2010 Sauter .................. B31F 1/07
425/363

* cited by examiner

METHOD FOR MANUFACTURING COMPOSITE SHEET

CROSS-REFERENCE TO RELATED APPLICATION

This is a divisional Application of Ser. No. 15/575,145 filed on Nov. 17, 2017, which is a National Phase of International Application No. PCT/JP2016/064428 filed on May 16, 2016, and claims priority from Japanese Application No. 2015-116142, filed Jun. 8, 2015, the disclosure of which is hereby incorporated by reference herein in its entirety.

TECHNICAL FIELD

The present invention relates to a method for manufacturing a composite sheet and, in particular, to a method of manufacturing a composite sheet constructed such that a first sheet and a second sheet are joined together.

BACKGROUND ART

In the conventional art, a technique has been proposed that a composite sheet having a recess-protrusion shape is employed as a front face sheet of an absorbing article caused to abut against the skin.

For example, in a composite sheet 7 shown in a sectional view of FIG. 9, a first sheet 3 and a second sheet 6 each squeezed between embossing rolls so that recesses and protrusions are formed are joined together by joining parts 8. In the first sheet 3, a depressed part 3b is formed along each joining part 8. Then, a protrusion 3a relatively protruding is formed in the surroundings thereof. In the second sheet 6, a protrusion 6a protruding opposite to the first sheet 3 side is formed along the joining part 8. Then, a depressed part 6b relatively depressed is formed in the other portion.

FIG. 10 is an explanation diagram of a device for manufacturing a composite sheet. As shown in FIG. 10, the device includes: a first roller 21 whose surface is provided with a large number of recess-shaped parts 24; a second roller 22 whose surface is provided with a large number of protrusion-shaped parts 25; and a third roller 23 whose surface is provided with a large number of recess-shaped parts 26. The first sheet 3 is caused to pass through between the first roller 21 and the second roller 22 so that emboss processing is performed by engagement between the recess-shaped parts 24 and the protrusion-shaped parts 25. Then, in a state that the first sheet 3 is held on the protrusion-shaped parts 25 of the second roller 22, the second sheet 6 is introduced to the outer periphery thereof and then these sheets 3 and 6 are caused to pass through between the second roller 22 and the third roller 23 so that emboss processing is performed by engagement between the protrusion-shaped parts 25 and the recess-shaped parts 26 and, at the same time, the joining parts 8 are formed in the tip parts of the protrusion-shaped parts 25 of the second roller 22 (for example, see Patent Document 1).

PRIOR ART DOCUMENT

Patent Document

Patent Document 1: Japanese Laid-Open Patent Publication No. 2013-248012

SUMMARY OF THE INVENTION

Problems to be Solved by the Invention

In the composite sheet 7 shown in FIG. 9, the first sheet 3 side abuts against the skin. Then, in the first sheet 3 and the second sheet 6, portions other than the joining parts 8 protrude toward the same side so as to be in a floating state so that a cushioning property is obtained.

Nevertheless, at the time that the first sheet 3 abuts against the skin so as to be crushed, the first sheet 3 is overlaid on the second sheet 6 and hence the feel against the skin easily becomes a hard feel. Nevertheless, when a soft construction material is employed in the sheets for the purpose of a soft feel, the recess-protrusion shape becomes easily crushed so that air permeability is degraded or, alternatively, a sticky feel is generated. Thus, it is difficult to realize a situation that the recess-protrusion shape is made crush-resistant in a state that the soft feel against the skin is maintained.

In view of such a practical situation, a problem to be solved by the present invention is to provide: a composite sheet whose recess-protrusion shape can easily be made crush-resistant in a state that the soft feel against the skin is maintained; and a device and a method for manufacturing said composite sheet.

Means for Solving the Problem

For the purpose of resolving the above-mentioned problem, the present invention provides a composite sheet constructed as follows.

A composite sheet includes: (a) a first sheet provided with a curved part in which one surface of the curved part rises and another surface of the curved part is recessed, and with a boundary part located adjacent to the curved part; and (b) a second sheet which is joined to the boundary part of the first sheet such as to cover the curved part of the first sheet so as to form a space in cooperation with the curved part and a region of which opposing the curved part is provided with a protruding part whose inner surface on the first sheet side rises such as to approach the curved part and whose outer surface on a side opposite to the first sheet is recessed and with a flat part surrounding the periphery of the protruding part.

In the above-mentioned configuration, when the construction materials of the first sheet and the second sheet, the sizes and the shapes of the curved part and the protruding part, and the like are selected, the space encompassing the surroundings of the protruding part can suitably be formed between the first sheet and the second sheet so that the feel obtained at the time that the one surface of the curved part of the first sheet abuts against the skin can easily be made soft. Further, at the time that the curved part of the first sheet is deformed, the curved part is supported by the protruding part of the second sheet. Then, when the flat part is provided in the surroundings of the protruding part of the second sheet, the protruding part can be made crush-resistant. Thus, in a state that the soft feel against the skin is maintained, the curved part of the first sheet can easily be made crush-resistant.

Preferably, a height of the protruding part measured from a surface of the flat part on the first sheet side is 30% or greater of a height of the other surface of the curved part measured from the surface of the flat part on the first sheet side.

In this case, the protruding part of the second sheet ensures the effect that the curved part of the first sheet is made crush-resistant.

Further, for the purpose of resolving the above-mentioned problem, the present invention provides a device for manufacturing a composite sheet constructed as follows.

A device for manufacturing a composite sheet includes: (a) a first roller which is provided with a cylinder-shaped first outer peripheral surface and with a recess retreating inward in a radial direction from the first outer peripheral surface and which revolves; and (b) a second roller which revolves in synchronization with the revolution of the first roller and which is provided with a cylinder-shaped second outer peripheral surface opposing the first outer peripheral surface and with a pressing part protruding outward in the radial direction from the second outer peripheral surface and then inserted into the recess of the first roller in a loose manner. In the device for manufacturing a composite sheet, in a state that a curved part of a first sheet provided with the curved part whose one surface rises and whose another surface is recessed and with a boundary part located adjacent to the curved part is accommodated in the recess of the first roller, that the boundary part is arranged along the first outer peripheral surface of the first roller, and that a second sheet is overlaid on the first sheet such as to cover the curved part, at the time that the first sheet and the second sheet pass through between the first roller and the second roller in association with the revolution of the first roller, the pressing part of the second roller pushes the second sheet into the recess so as to cause deformation, whereby in a region within the second sheet opposing the curved part, a protruding part can be formed which is surrounded by a flat part and in which an inner surface thereof on the first sheet side rises such as to approach the curved part and an outer surface thereof on a side opposite to the first sheet is recessed.

In the above-mentioned configuration, the pressing part of the second roller is inserted into the recess of the first roller in a loose manner. Thus, a space is formed between the curved part of the first sheet and the second sheet and then a flat part and a protruding part surrounded by the flat part can be formed in a region within the second sheet opposing the curved part.

The above-mentioned configuration permits continuous manufacture of a composite sheet whose recess-protrusion shape can easily be made crush-resistant in a state that the soft feel against the skin is maintained.

Preferably, the device for manufacturing a composite sheet further includes (c) a first heating part for heating the pressing part.

In this case, the second sheet can be deformed in a heated state by the pressing part so that the protruding part can easily be formed in the second sheet.

Preferably, the device for manufacturing a composite sheet further includes: (d) a third roller which is provided with a cylinder-shaped third outer peripheral surface opposing the first outer peripheral surface and which revolves in synchronization with the first roller; and (e) a second heating part for heating any one or both of the first roller and the third roller. In the device for manufacturing a composite sheet, the first sheet and the second sheet pass through between the first roller and the third roller in a state of being squeezed and heated between the first roller and the third roller so that the boundary part of the first sheet can be joined to the second sheet.

In this case, the boundary part of the first sheet can be joined to the second sheet at any one or both of timings prior and posterior to the timing that the pressing part is pushed into the second sheet.

Preferably, the device for manufacturing a composite sheet further includes (f) a fourth roller which revolves in synchronization with the revolution of the first roller and which is provided with a cylinder-shaped fourth outer peripheral surface opposing the first outer peripheral surface and with a protrusion protruding outward in the radial direction from the fourth outer peripheral surface and then inserted into the recess of the first roller. In the device for manufacturing a composite sheet, at the time that the first sheet in a not-yet processed state before the curved part and the boundary part are formed is arranged along the first outer peripheral surface such as to cover the recess of the first roller and then the first sheet passes through between the first roller and the fourth roller in association with the revolution of the first roller, the protrusion of the fourth roller pushes the first sheet into the recess so as to cause deformation so that the curved part and the boundary part are formed in the first sheet.

In this case, the curved part, the boundary part, and the recess can be formed by using the first sheet in a not-yet processed state.

Further, for the purpose of resolving the above-mentioned problem, the present invention provides a method for manufacturing a composite sheet constructed as follows.

A method for manufacturing a composite sheet includes: (i) a first step of, in a state that a curved part of a first sheet provided with the curved part whose one surface rises and whose another surface is recessed and with a boundary part located adjacent to the curved part is accommodated in a recess retreating inward in a radial direction from an outer peripheral surface of a first roller, that the boundary part is arranged along the outer peripheral surface of the first roller, and that a second sheet is overlaid on the first sheet such as to cover the curved part, revolving the first roller so as to convey the first sheet and the second sheet; (ii) a second step of, by a method that the first sheet and the second sheet conveyed during the first step are caused to pass through between the first roller and the second roller and, at the same time, the second roller is caused to revolve in synchronization with the first roller so that a pressing part protruding outward in the radial direction from the outer peripheral surface of the second roller is inserted into the recess of the first roller in a loose manner and thereby the pressing part of the second roller pushes the second sheet into the recess so as to cause deformation, forming, in a region within the second sheet opposing the curved part, a protruding part which is surrounded by a flat part and in which an inner surface thereof on the first sheet side rises such as to approach the curved part and an outer surface thereof on a side opposite to the first sheet is recessed; and (iii) a third step of joining the boundary part of the first sheet to the second sheet at least at any one selected from timings prior to the second step, posterior to the second step, and simultaneous to the second step.

In the above-mentioned method, the pressing part is inserted into the recess of the first roller in a loose manner. Thus, a protruding part encompassed by a flat part can be formed in the second sheet.

The above-mentioned method permits continuous manufacture of a composite sheet which provides a soft feel against the skin and in which the recess-protrusion shape of the surface can easily be made crush-resistant.

Preferably, at the second step, the pressing part of the second roller is in a heated state.

In this case, the second sheet can be deformed in a heated state by the pressing part so that the protruding part can easily be formed in the second sheet.

Preferably, at the third step, the first sheet and the second sheet conveyed during the first step are caused to pass through between the first roller and the third roller and thereby the first sheet and the second sheet are squeezed and heated between the first roller and the third roller so that the boundary part of the first sheet is joined to the second sheet.

In this case, the first sheet and the second sheet can be joined together by using the first roller.

The method for manufacturing a composite sheet further includes (iv) a fourth step of, at a timing prior to the first step, by a method that the first sheet in a not-yet processed state before the curved part and the boundary part are formed is passed through between the first roller and a fourth roller in a state of being arranged along the first outer peripheral surface such as to cover the recess of the first roller and, at the same time, the fourth roller is caused to revolve in synchronization with the first roller so that a protrusion protruding outward in the radial direction from the outer peripheral surface of the fourth roller is inserted into the recess of the first roller and thereby the protrusion of the fourth roller pushes the first sheet into the recess so as to cause deformation, forming the curved part and the boundary part in the first sheet.

In this case, the curved part and the boundary part can be formed by using the first sheet in a not-yet processed state.

Advantage of the Invention

According to the present invention, in a composite sheet, the recess-protrusion shape can easily be made crush-resistant in a state that the soft feel against the skin is maintained.

MODE OF CARRYING THE INVENTION

Embodiments serving as the mode of implementing the present invention are described below with reference to the drawings.

First Embodiment

A composite sheet 50 of a first embodiment is described below with reference to FIGS. 1 to 4.

Figure 1:
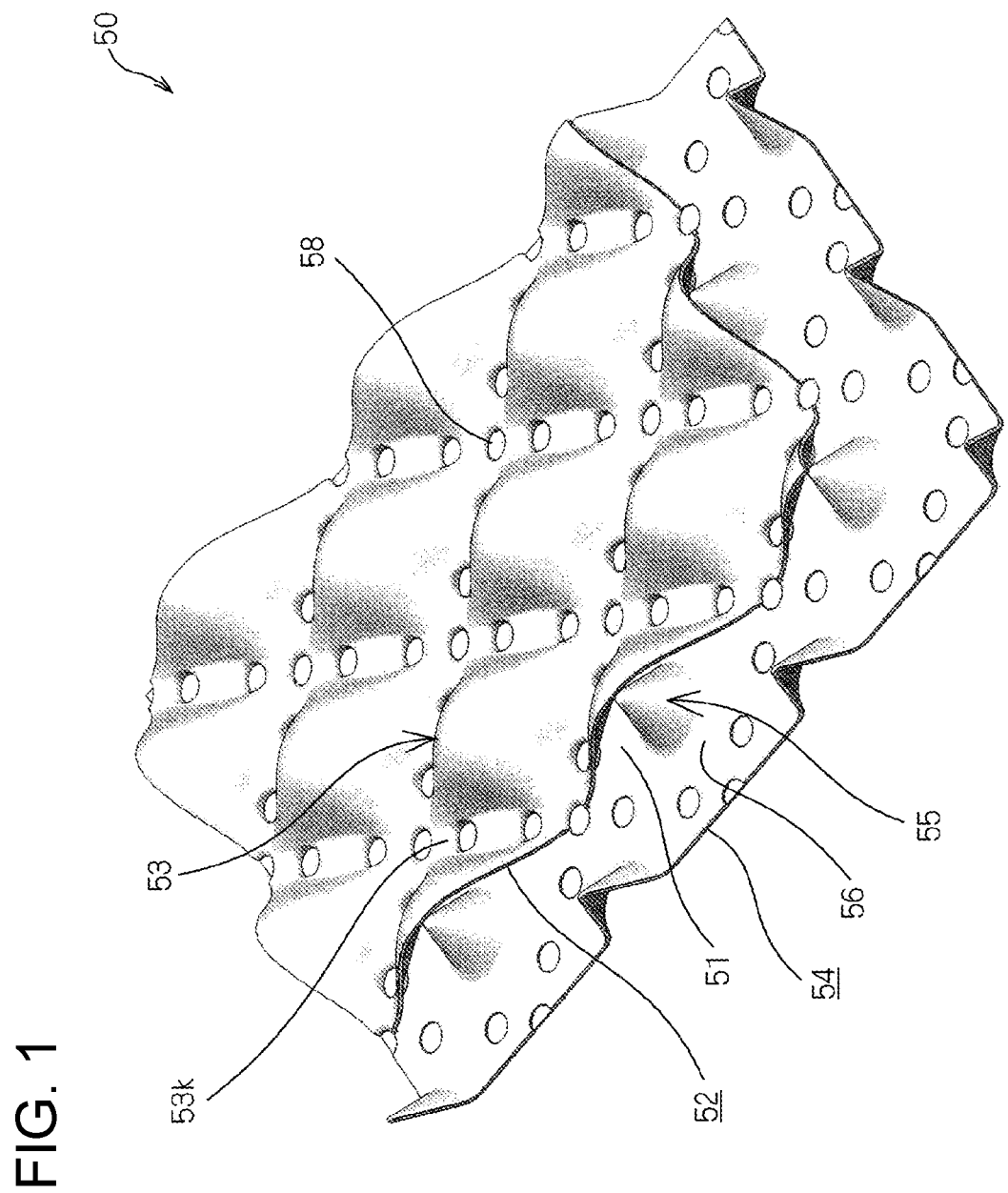
FIG. 1 is a conceptual diagram of a composite sheet (First Embodiment).
Figure 2:
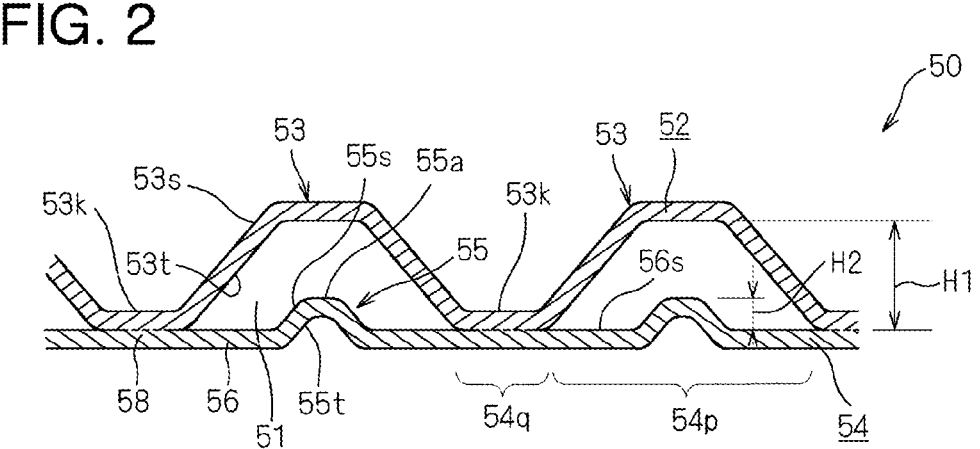
FIG. 2 is a main part sectional view of the composite sheet (First Embodiment).

FIG. 1 is a conceptual diagram of the composite sheet 50. FIG. 2 is a main part sectional view of the composite sheet 50. As shown in FIGS. 1 and 2, in the composite sheet 50, a first sheet 52 and a second sheet 54 are joined together. The first and the second sheet 52 and 54 may be fabricated from suitably selected materials. The construction materials of the first and the second sheet 52 and 54 may be the same as each other or, alternatively, may be different from each other. Preferably, the first and the second sheet 52 and 54 are fabricated from a material capable of being deformed or welded by heating like a nonwoven fabric containing a resin material. For example, the composite sheet 50 can be utilized as a front face sheet of an absorbing article such as a sanitary napkin, an incontinence pad, and a disposable diaper caused to abut against the skin.

The first sheet 52 is provided with a curved part 53 in which one surface 53s thereof rises and the other surface 53t thereof is recessed and with a boundary part 53k located adjacent to the curved part 53. FIG. 1 shows an example that the curved parts 53 are arranged in a lattice form. However, the curved parts may be arranged in another pattern such as a zigzag form and a honeycomb form. Alternatively, plural kinds of curved parts having different shapes or sizes from each other may be arranged.

The second sheet 54 is joined to the boundary part 53k of the first sheet 52 such as to cover the curved part 53 of the first sheet 52 so as to form a space 51 in cooperation with the curved part 53. Although details are described later, joined parts 58 each joining each boundary part 53k of the first sheet 52 to the second sheet 54 are intermittently formed by hot welding or the like. Here, the boundary part 53k of the first sheet 52 may be joined to the second sheet 54 by a method other than hot welding, like by ultrasonic welding or by gluing with adhesives. In place of the intermittent forming of the joined parts 58, a joined part extending continuously along the boundary part 53k of the first sheet 52 may be formed. Employable shapes for the joined part 58 are not limited to a circle shown in the figure. That is, a suitable shape may be selected like a rectangle, a cross shape, and a star shape.

In the second sheet 54, a protruding part 55 and a flat part 56 are formed in a region 54p opposing the curved part 53 of the first sheet 52. In the protruding part 55, an inner surface 55s thereof on the first sheet 52 side rises such as to approach the curved part 53 and an outer surface 55t thereof on a side opposite to the first sheet 52 is recessed. The flat part 56 encompasses the protruding part 55 and extends flat together with a region 54q within the second sheet 54 opposing the boundary part 53k of the first sheet 52. The space 51 encompasses the surroundings of the protruding part 55.

FIGS. 1 and 2 show an example that a tip 55a of the protruding part 55 of the second sheet 54 is located distant from the curved part 53 of the first sheet 52. Instead, a configuration shown in FIGS. 3 and 4 may be employed.

Figure 3:
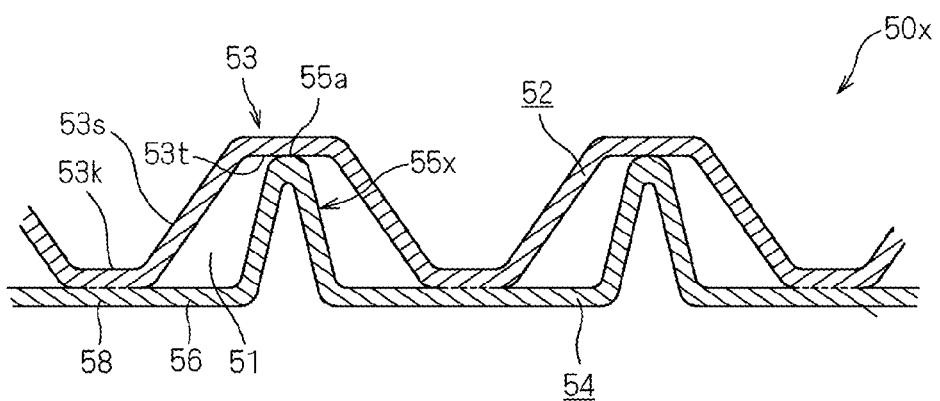
FIG. 3 is a main part sectional view of a composite sheet (First Modification of First Embodiment).
Figure 4:
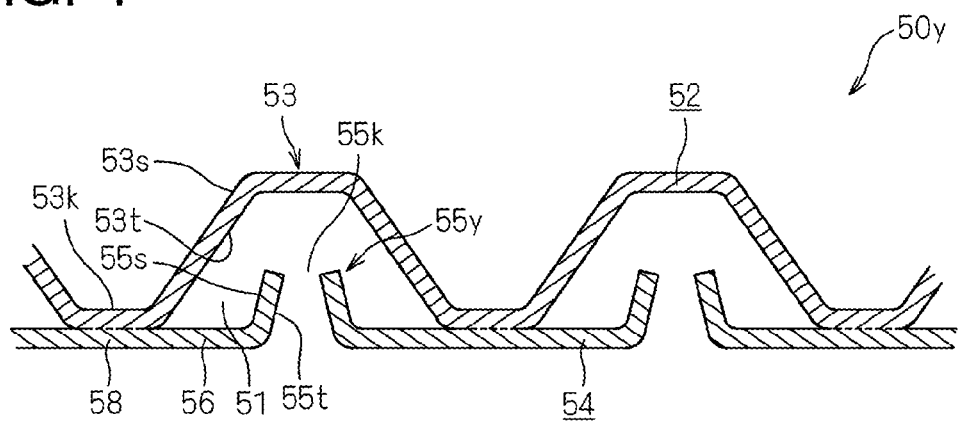
FIG. 4 is a main part sectional view of a composite sheet (Second Modification of First Embodiment).

FIGS. 3 and 4 are main part sectional views of composite sheets 50x and 50y whose protruding parts 55x and 55y individually serve as modifications. As shown in FIG. 3, the tip 55a of the protruding part 55x may be in contact with the other surface 53t of the curved part 53 of the first sheet. Further, as shown in FIG. 4, an opening part 55k may be formed at the tip of the protruding part 55y.

In each composite sheet 50, 50x, or 50y, when the construction materials of the first and the second sheet 52 and 54, the sizes and the shapes of the curved part 53 and the protruding part 55, 55x, or 55y, and the like are selected, the space 51 encompassing the surroundings of the protruding part 55, 55x, or 55y can suitably be formed between the first sheet 52 and the second sheet 54 so that the feel obtained at the time that the rising one surface 53s of the curved part 53 of the first sheet 52 abuts against the skin can easily be made soft. Further, at the time that the curved part 53 of the first sheet 52 is deformed, the curved part 53 is supported by the protruding part 55, 55x, or 55y of the second sheet 54. Then, when the flat part 56 is provided in the surroundings of the protruding part 55, 55x, or 55y of the second sheet 54, the protruding part 55, 55x, or 55y can be made crush-resistant. Thus, in the composite sheet 50, 50x, or 50y, the recess-protrusion shape shape can easily be made crush-resistant in a state that the soft feel against the skin is maintained.

As shown in FIG. 2, when the height measured from a surface 56s of the flat part 56 on the first sheet 52 side to the other surface 53t of the curved part 53 is denoted by H1 and the height measured from the surface 56s of the flat part 56 of the second sheet 54 on the first sheet 52 side to the protruding part 55 is denoted by H2, it is preferable that H2≥0.3×H1 is satisfied.

In this case, the protruding part 55 of the second sheet 54 ensures the effect that the curved part 53 of the first sheet 52 is made crush-resistant.

Second Embodiment

Next, a device 10 for manufacturing a composite sheet of a second embodiment (simply referred to as a "manufacturing device 10" in some cases in the following description) and a method for manufacturing a composite sheet are described below with reference to FIGS. 5 to 8. The composite sheet 50 of the first embodiment can be fabricated by using the device 10 of the second embodiment.

Figure 5:
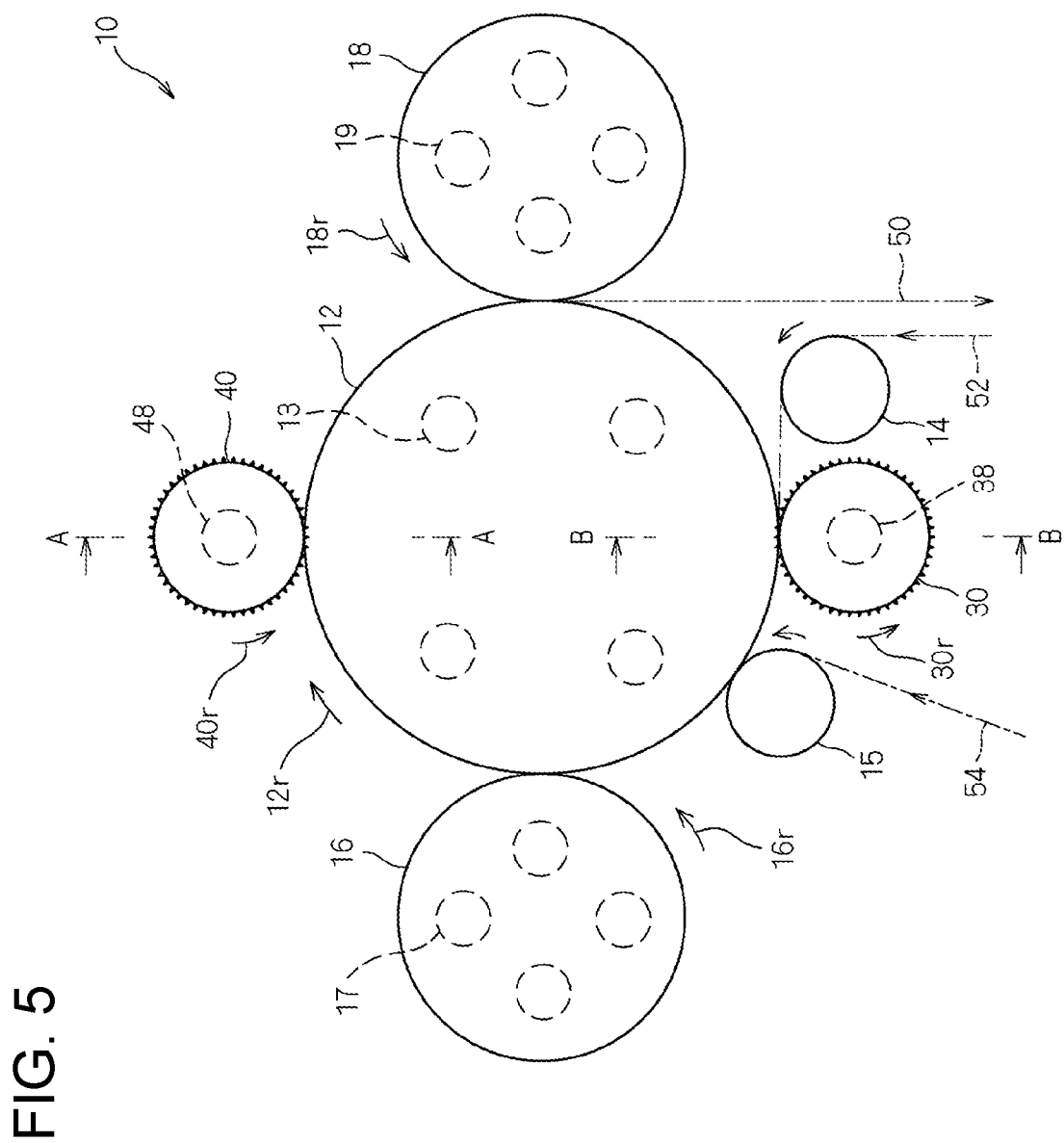
FIG. 5 is an explanation diagram of a device for manufacturing a composite sheet (Second Embodiment).
Figure 6:
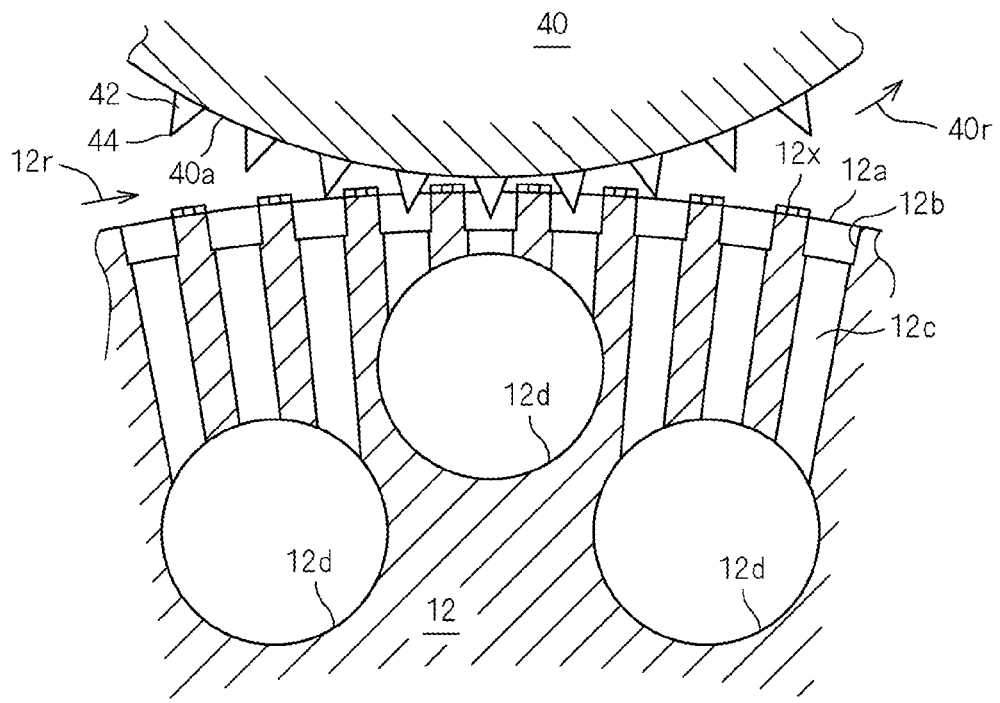
FIG. 6 is a main part sectional view of the device for manufacturing a composite sheet (Second Embodiment).
Figure 7:
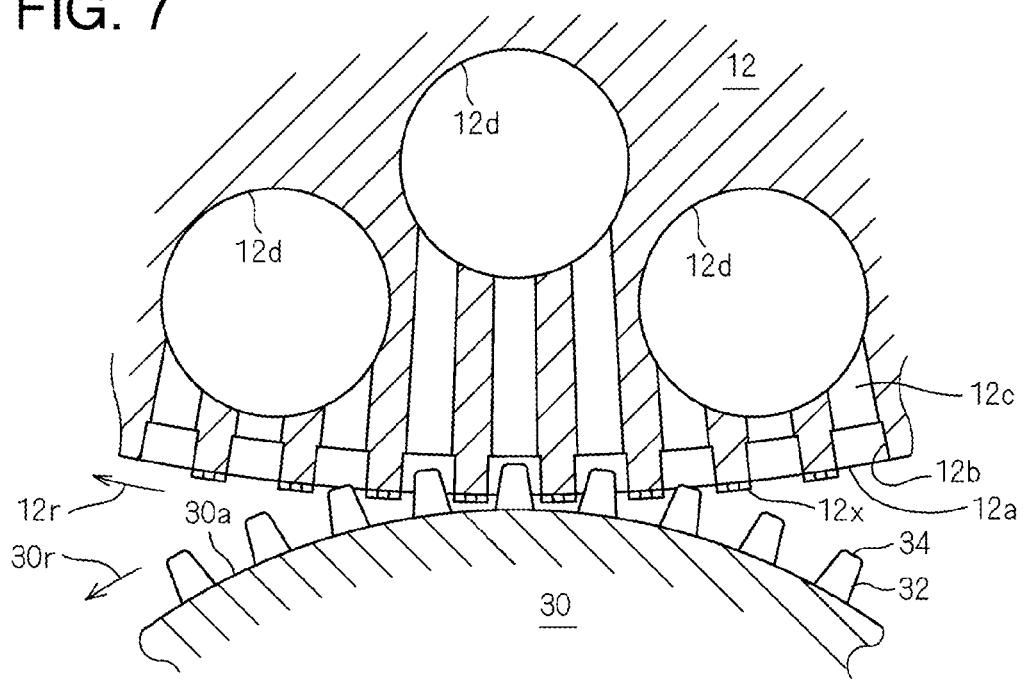
FIG. 7 is a main part sectional view of the device for manufacturing a composite sheet (Second Embodiment).

FIG. 5 is an explanation diagram of the device 10 for manufacturing a composite sheet. FIG. 6 is a main part sectional view taken along a straight line A-A in FIG. 5. FIG. 7 is a main part sectional view taken along a straight line B-B in FIG. 5.

As shown in FIG. 5, a first shaping roller 30, a first seal roller 16, a second shaping roller 40, and a second seal roller 18 are arranged evenly, that is, at every 90°, in the surroundings of the first roller 12. The first and the second shaping roller 30 and 40 are arranged symmetrically with respect to the first roller 12 and the first and the second seal roller 16 and 18 are arranged symmetrically with respect to the first roller 12. These individual rollers 12, 16, 18, 30, and 40 are driven so as to revolve in synchronization with each other in the directions of arrows 12r, 16r, 18r, 30r, and 40r. Heaters 13, 17, 19, 38, and 48 schematically shown in the figure and serving as the heating parts are built in the individual rollers 12, 16, 18, 30, and 40.

Here, a configuration may be employed that the first and the second seal roller 16 and 18 or the first and the second shaping roller 30 and 40 are arranged not evenly with respect to the first roller 12.

The second shaping roller 40 corresponds to the "second roller" of the present invention. The heater 48 built in the second shaping roller 40 corresponds to the "first heating part" of the present invention. The first and the second seal roller 16 and 18 correspond to the "third roller" of the present invention. The heater 13 built in the first roller 12 and the heaters 17 and 19 built in the first and the second seal roller 16 and 18 correspond to the "second heating part" of the present invention. The first shaping roller 30 corresponds to the "fourth roller" of the present invention.

Further, arranged in the surroundings of the first roller 12 are: a first guiding roller 14 for introducing the first sheet 52 along the outer peripheral surface of the first roller 12; a second guiding roller 15 for introducing the second sheet 54 onto the first sheet 52 extending along the outer peripheral surface of the first roller.

The first sheet 52 having been introduced along the outer peripheral surface of the first roller 12 is conveyed in association with the revolution of the first roller 12 so as to pass through between the first roller 12 and the first shaping roller 30. After that, the second sheet 54 is overlaid onto the first sheet 52. After that, the first and the second sheet 52 and 54 pass through between the first roller 12 and the first seal roller 16, then between the first roller 12 and the second shaping roller 40, and then between the first roller 12 and the second seal roller 18 so as to be conveyed from the first roller 12 to the outside in the form of the composite sheet 50.

As shown in FIGS. 6 and 7, the first roller 12 is provided with: recesses 12b retreating inward in the radial direction from a cylinder-shaped outer peripheral surface 12a of the first roller 12; suction passages 12c and 12d in fluid communication with the bottom of each recess 12b; and cylinder-shaped seal protrusions 12x protruding outward in the radial direction from the outer peripheral surface 12a of the first roller 12. The outer peripheral surface 12a of the first roller 12 corresponds to the "first outer peripheral surface" of the present invention.

Figure 8:
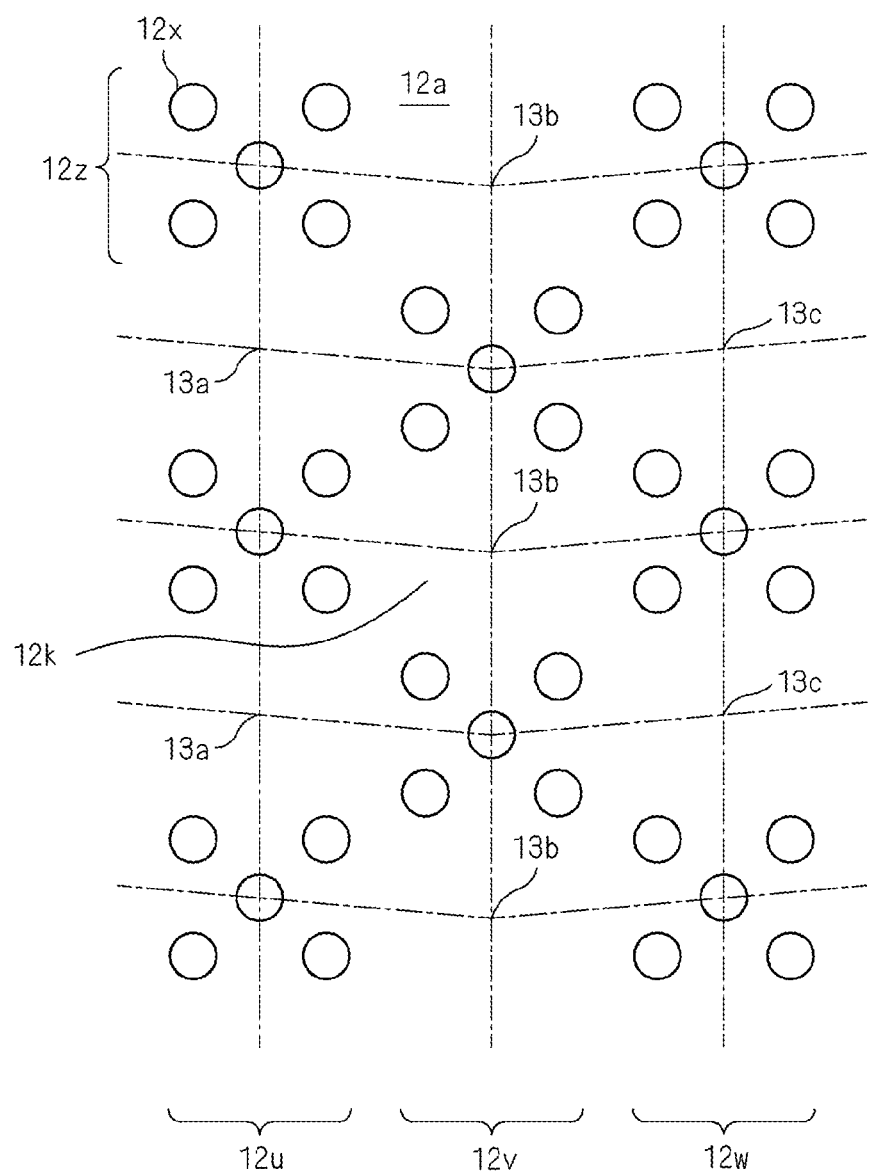
FIG. 8 is a main part development view of an outer peripheral surface of a first roller (Second Embodiment).
Figure 9:
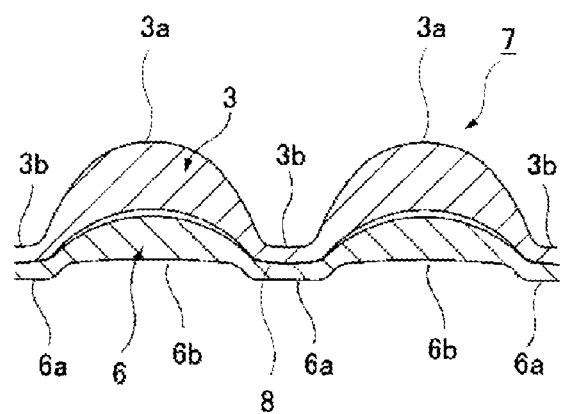
FIG. 9 is a main part sectional view of a composite sheet (First Conventional Example).
Figure 10:
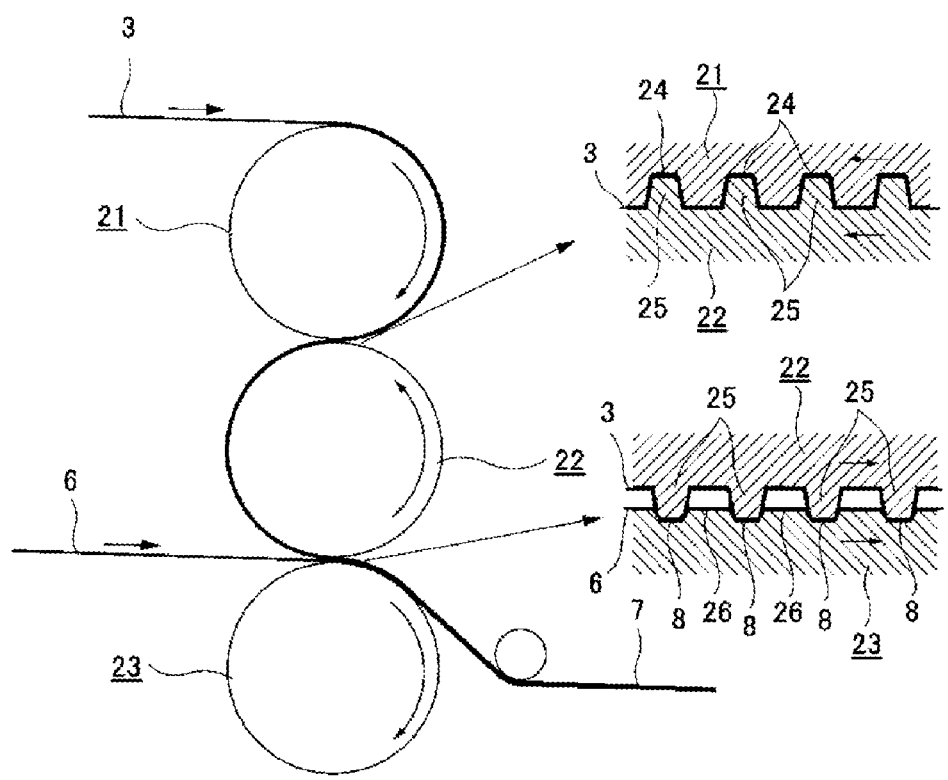
FIG. 10 is an explanation diagram of a device for manufacturing the composite sheet (First Conventional Example).

FIG. 8 is a main part development view of the outer peripheral surface 12a of the first roller 12. The seal protrusions 12x grouped into five pieces each as indicated by numeral 12z in FIG. 8 are provided at regular intervals in the axial direction of the first roller 12 (in the up and down directions in FIG. 8). Columns 12u to 12w along each of which the groups 12z of the seal protrusions 12x are aligned in the axial direction are arranged adjacent to each other in the circumferential direction of the first roller 12 (in the right and left directions in FIG. 8) in a state of being deviated by approximately a half pitch. The recess (not shown in FIG. 8) formed in the first roller 12 is located in the inside of a substantially rhombus-shaped region 12k encompassed by the 12 seal protrusions 12x aligned in a substantially rhombus shape. The center position of the recess agrees with each middle point 13a to 13c of each of the groups 12z of the seal protrusions 12x arranged adjacent to each other in the axial direction.

As shown in FIG. 7, the first shaping roller 30 is provided with protrusions 32 which protrude outward in the radial direction from a cylinder-shaped outer peripheral surface 30a of the first shaping roller 30 in correspondence to the recesses 12b of the first roller 12 and each of which has a truncated pyramid shape whose tip 34 is flat. The shape of each protrusion 32 of the first shaping roller 30 may be other than the truncated pyramid shape. That is, a rectangular parallelepiped shape, a cylinder-shaped, or the like may be employed. The outer peripheral surface 30a of the first shaping roller 30 corresponds to the "fourth outer peripheral surface" of the present invention. When the first roller 12 and the first shaping roller 30 revolve in synchronization with each other, each protrusion 32 of the first shaping roller 30 enters each recess 12b of the first roller 12. At that time, the protrusion 32 of the first shaping roller 30 heats and pushes a portion which is located within the first sheet (not shown in FIG. 7) arranged along the outer peripheral surface 12a of the first roller 12 and which covers the recess 12b of the first roller 12, into the recess 12b of the first roller 12 so as to cause deformation and thereby forms the curved part in the first sheet. In order that the curved part may be formed in a heated state, it is preferable that a material containing a resin material is employed for the first sheet 52 and that the heating temperature is set lower than the melting temperature of the resin material in the first sheet 52.

The recesses 12b of the first roller 12 are connected through the suction passages 12c and 12d to a negative pressure source. By virtue of this, the first sheet arranged along the outer peripheral surface 12a of the first roller 12 is held by suction along the outer peripheral surface 12a of the first roller 12 so that the curved parts formed in the first sheet are maintained in a state of being accommodated in the recesses 12b.

As shown in FIG. 6, the second shaping roller 40 is provided with cone-shaped pressing parts 42 protruding outward in the radial direction from the cylinder-shaped outer peripheral surface 40a in correspondence to the recesses 12b of the first roller 12. The outer peripheral surface 40a of the second shaping roller 40 corresponds to the "second outer peripheral surface" of the present invention. The tip 44 of each pressing part 42 may be sharp or round. At the time that the first roller 12 and the second shaping roller 40 revolve in synchronization with each other, the pressing parts 42 are inserted into the recesses 12b of the first roller 12 in a loose manner.

By virtue of this, at the time that the first and the second sheet (not shown in FIG. 6) arranged along the outer peripheral surface 12a of the first roller 12 pass through between the first roller 12 and the second shaping roller 40, each pressing part 42 of the second shaping roller 40 heats and pushes the center part of a region within the second sheet opposing the curved part of the first sheet, toward the curved part side of the first sheet so as to deform the second sheet and thereby forms the protruding part. In order that the protruding part may be formed in a heated state, it is preferable that a material containing a resin material is employed for the second sheet 54 and that the heating temperature is set lower than the melting temperature of the resin material in the second sheet 54.

In a case that the tip 44 of the pressing part 42 breaks through the second sheet when the pressing part 42 of the second shaping roller 40 is pushed into the second sheet, the protruding part 55y can be formed in which the opening part 55k is formed at the tip thereof as shown in FIG. 4 given above.

The pressing parts 42 of the second shaping roller 40 are inserted into the recesses 12b of the first roller 12 in a loose manner. Thus, as shown in FIGS. 1 and 2, each protruding part 55 is formed in the center part of a region within the second sheet 54 opposing the curved part 53 of the first sheet 52 so that the surroundings of the protruding part 55 is surrounded by the flat part 56.

As shown in FIG. 5, in the first and the second seal roller 16 and 18, at the time that the first and the second sheet 52 and 54 arranged along the outer peripheral surface of the first roller 12 pass through between the first roller 12 and the first or the second seal roller 16 or 18, the first and the second sheet 52 and 54 are squeezed and heated between the cylinder-shaped outer peripheral surface of the first or the second seal roller 16 or 18 and each seal protrusion 12x (see FIGS. 6 and 7) of the first roller 12 so that the first and the second sheet 52 and 54 are hot welded and thereby the joined part 58 (see FIGS. 1 to 4) for joining the first and the second sheet 52 and 54 is formed. The outer peripheral surfaces of the first and the second seal roller 16 and 18 correspond to the "third outer peripheral surface" of the present invention.

When the hot welding between the first and the second sheet 52 and 54 is repeated by using the first and the second seal roller 16 and 18, the first and the second sheet 52 and 54 can reliably be joined together in a state that formation of an undesired hole is avoided in the joined part 58 of the first and the second sheet 52 and 54.

Here, in the example given above, two seal rollers have been employed. Instead, one or three or more seal rollers may be employed. Alternatively, as described later, the first and the second seal roller 16 and 18 may be omitted. In a case that the first sheet in which the curved parts are formed in advance is employed, the first shaping roller 30 may be omitted.

In place of a configuration that the heaters 38 and 48 are built in the first and the second shaping roller 30 and 40, the protrusions 32 of the first shaping roller 30 and the pressing parts 42 of the second shaping roller 40 may be heated by heating parts constructed from heaters or the like provided in the outside of the first and the second shaping roller 30 and 40.

In place of a configuration that the seal protrusions 12x are formed in the first roller 12, seal protrusions may be formed in the outer peripheral surfaces of the first and the second seal roller 16 and 18. Alternatively, seal protrusions may be formed in both of the first roller 12 and the first and the second seal roller 16 and 18.

Next, process steps of fabricating the composite sheet 50 by using the manufacturing device 10 are described below with reference to FIGS. 5 to 7.

(1) First, the curved parts of the first sheet 52 are accommodated into the recesses 12b of the first roller 12 and then the boundary parts of the first sheet 52 are aligned with the outer peripheral surface 12a of the first roller 12. Further, in a state that the second sheet 54 containing a resin material is overlaid onto the first sheet 52 so as to cover the curved parts of the first sheet 52, the first roller 12 is revolved so that the first and the second sheet 52 and 54 are conveyed.

(1-1) Specifically, the first sheet 52 guided by the first guiding roller 14 is arranged along the outer peripheral surface 12a of the first roller 12 and then caused to pass through between the first roller 12 and the first shaping roller 30. Further, the first shaping roller 30 is caused to revolve in synchronization with the first roller 12 and then the protrusions 32 of the first shaping roller 30 are inserted into the recesses 12b of the first roller 12. At that time, in the first sheet 52, the heated protrusions 32 of the first shaping roller 30 are pushed into the portions covering the recesses 12b of the first roller 12 so as to cause deformation so that the curved parts are formed in the first sheet 52. At that time, each portion within the first sheet 52 surrounding the curved part and extending along the outer peripheral surface 12a of the first roller 12 constitutes the boundary part.

(1-2) The first sheet 52 is conveyed in a state that the curved parts thereof are accommodated in the recesses 12b of the first roller 12. The second sheet 54 guided by the second guiding roller 15 is overlaid onto the first sheet 52 such as to cover the curved parts of the first sheet 52 and then the first and the second sheet 52 and 54 are conveyed in association with the revolution of the first roller 12.

(2) Then, the first and the second sheet 52 and 54 are caused to pass through between the first roller 12 and the first seal roller 16 and thereby the first and the second sheet 52 and 54 are squeezed and heated between each seal protrusion 12x of the first roller 12 and the outer peripheral surface of the first seal roller 16 so that the boundary parts of the first sheet 52 are joined to the second sheet 54.

(3) Then, the first and the second sheet 52 and 54 are caused to pass through between the first roller 12 and the second shaping roller 40 and, at the same time, the second shaping roller 40 is caused to revolve in synchronization with the first roller 12 so that the pressing parts 42 of the second shaping roller 40 are inserted into the recesses 12b of the first roller 12 in a loose manner. By virtue of this, the heated pressing parts 42 of the second shaping roller 40 heat and push the second sheet 54 into the recesses 12b such as to deform the second sheet 54 so that each protruding part whose inner surface on the first sheet 52 side rises such as to approach the curved part and whose outer surface on a side opposite to the first sheet 52 is recessed is formed in the center part of each region within the second sheet 54 opposing each curved part of the first sheet 52. Since the protruding part is formed only in the center part of a region opposing the curved part of the first sheet 52, the protruding part is surrounded by the flat part of the second sheet 54.

(4) Then, the first and the second sheet 52 and 54 are caused to pass through between the first roller 12 and the second seal roller 18 and thereby the first and the second sheet 52 and 54 are squeezed and heated between each seal protrusion 12x of the first roller 12 and the outer peripheral surface of the second seal roller 18 so that the boundary parts of the first sheet 52 are further joined to the second sheet 54.

(5) Then, the first and the second sheet 52 and joined together, that is, the composite sheet 50, is conveyed from the first roller 12 to the outside.

As a result of the above-mentioned process steps, the composite sheet 50 can be fabricated.

The above-mentioned process step (1-2) corresponds to the "first step" of the present invention. The above-mentioned process steps (2) and (4) correspond to the "third step" of the present invention. The above-mentioned process step (3) corresponds to the "second step" of the present invention. The above-mentioned process step (1-1) corresponds to the "fourth step" of the present invention.

As a result of the above-mentioned process steps (2) and (4), the first and the second sheet 52 and 54 can be joined together by using the first roller 12. Any one alone of the above-mentioned process steps (2) and (4) may be employed. In this case, the one of the first and the second seal roller 16 and 18 can be omitted.

After the first sheet 52 and the second sheet 54 are joined together at the above-mentioned process step (2), when the protruding parts are formed in the second sheet at the above-mentioned process step (3), positioning between the curved parts of the first sheet and the protruding parts of the second sheet becomes easy.

The above-mentioned process steps (2) and (4) may be omitted so that the first and the second sheet 52 and 54 may be conveyed from the first roller 12 to the outside in a state of being not yet joined together and, after that, the boundary parts of the first sheet 52 may be joined to the second sheet 54 by using another device.

Simultaneously to the above-mentioned process step (3), the first and the second sheet 52 and 54 may be squeezed and heated between the outer peripheral surface 12a of the first roller 12 and the outer peripheral surface 40a of the second shaping roller 40 so that the boundary parts of the first sheet 52 may be joined to the second sheet 54. This indicates that the "third step" of the present invention is achieved simultaneously to the "second step" of the present invention. Thus, the first and the second seal roller 16 and 18 can be omitted.

Further, in place of the above-mentioned process steps (1-1) and (1-2), in a state that the boundary parts of a first sheet in which the curved parts are formed in advance are arranged along the outer peripheral surface 12a of the first roller 12, that the curved parts of the first sheet are accommodated into the recesses 12b of the first roller 12, and that the second sheet is overlaid onto the first sheet such that the curved parts are covered by the second sheet, the first and the second sheet may be conveyed in synchronization with the revolution of the first roller 12. In this case, even a first sheet not containing a resin material may be employed.

Suitable selection may be made on: the shapes and the sizes of the recesses 12b of the first roller 12, the protrusions 32 of the first shaping roller 30, and the pressing parts 42 of the second shaping roller 40; the revolution rates of the individual rollers 12, 16, 18, 30, and 40 (the conveyance rate of the first and the second sheet 52 and 54); the temperatures of the protrusion 32 and the pressing part 42; the construction materials of the first and the second sheet 52 and 54; and the like. Then, by using the manufacturing device 10, a composite sheet can be fabricated in which the recess-protrusion shape is not easily crushed in a state that the soft feel against the skin is maintained.

CONCLUSION

In the composite sheet 50 described above, the recess-protrusion shape can easily be made crush-resistant in a state that the soft feel against the skin is maintained.

Here, the present invention is not limited to the embodiments given above and may be implemented with various changes.

For example, the composite sheet of the present invention may be employed as a front face sheet of an article caused to abut against the skin other than an absorbing article or, alternatively, may be employed as a sheet other than a front face sheet caused to abut against the skin.

DESCRIPTION OF REFERENCE DESIGNATIONS

10 Device for manufacturing a composite sheet
12 First roller
12a Outer peripheral surface (first outer peripheral surface)
12b Recess
13 Heater (second heating part)
16 First seal roller (third roller)
17 Heater (second heating part)
18 Second seal roller (third roller)
19 Heater (second heating part)
30 First shaping roller (fourth roller)
30a Outer peripheral surface (fourth outer peripheral surface)
40 Second shaping roller (second roller)
40a Outer peripheral surface (second outer peripheral surface)
42 Pressing part
48 Heater (first heating part)
50, 50x, 50y Composite sheet
51 Space
52 First sheet
53 Curved part
53k Boundary part
53s One surface
53t The other surface
54 Second sheet
54p Region opposing curved part
55, 55x, 55y Protruding part
55s Inner surface
55t Outer surface
56 Flat part
56s Surface on first sheet side

The invention claimed is:
1. A method for manufacturing a composite sheet, comprising, in this order:

rotating a first roller with a recess retreating inward in a radial direction from an outer peripheral surface thereof, so as to convey a first sheet having a curved part with one surface raised and another surface recessed, and a boundary part located adjacent to the curved part, the curved part being accommodated in the recess of the first roller and the boundary part being arranged along the outer peripheral surface of the first roller;

providing a second sheet over the first sheet to cover the curved part of the first sheet;

conveying the first and second sheets along the outer peripheral surface of the first roller while rotating the first roller;

rotating a second roller having a pressing part protruding outward in a radial direction from an outer peripheral surface thereof, in synchronization with the first roller to pass the first sheet and the second sheet between the first roller and the second roller such that the pressing part of the second roller is inserted into the recess of the first roller in a loose manner to push the second sheet into the recess so as to form, in a region within the second sheet opposing the curved part of the first sheet, a protruding part which is surrounded by a flat part and in which an inner surface of the second sheet on a first sheet side rises to approach the curved part of the first sheet and an outer surface of the second sheet on a side opposite to the first sheet is recessed; and joining the boundary part of the first sheet to the second sheet before or after or at a same time of forming the protruding part.

2. The method for manufacturing a composite sheet according to claim 1, wherein the pressing part of the second roller is heated.

3. The method for manufacturing a composite sheet according to claim 1, wherein the first sheet and the second sheet are conveyed to pass through between the first roller and a third roller and thereby the first sheet and the second sheet are squeezed and heated between the first roller and the third roller so that the boundary part of the first sheet is joined to the second sheet.

4. The method for manufacturing a composite sheet according to claim 1, further comprising passing the first sheet without having the curved part and the boundary part between the first roller and a fourth roller with a protrusion protruding outward in a radial direction from an outer peripheral surface thereof, along the outer peripheral surface of the first roller to cover the recess of the first roller while rotating the fourth roller in synchronization with the first roller so that the protrusion of the fourth roller is inserted into the recess of the first roller and thereby the protrusion of the fourth roller pushes the first sheet into the recess so as to cause deformation, forming the curved part and the boundary part in the first sheet.

* * * * *